Figure 1:
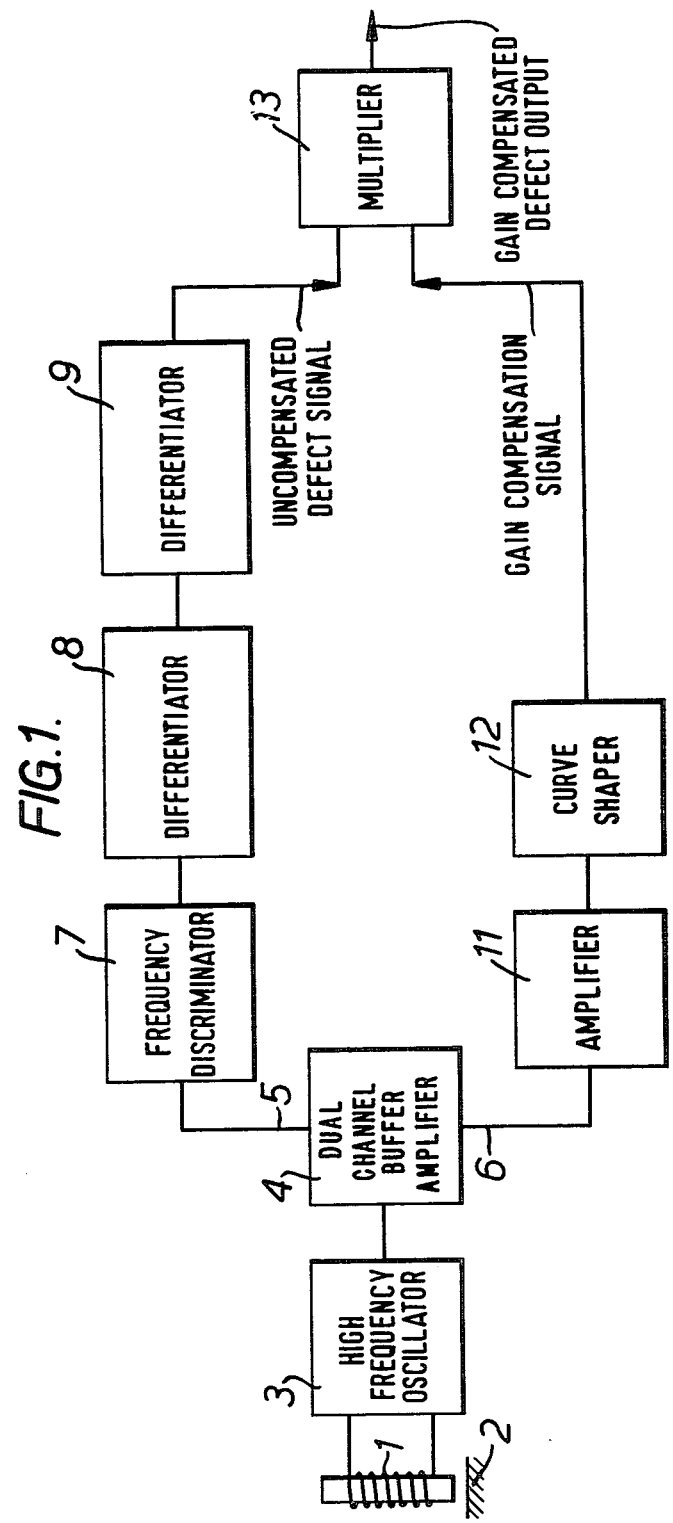

United States Patent [19]

Savidge et al.

[11] 4,274,054
[45] Jun. 16, 1981

[54] DUAL CHANNEL APPARATUS FOR DETECTING SURFACE DEFECTS IN ELONGATE METALLIC MEMBERS WITH LIFTOFF COMPENSATION

[75] Inventors: David H. Savidge, Rotherham; Eric Wadsworth, Sheffield, both of England

[73] Assignee: British Steel Corporation, London, England

[21] Appl. No.: 962,945

[22] Filed: Nov. 22, 1978

[30] Foreign Application Priority Data

Nov. 22, 1977 [GB] United Kingdom ............... 48597/77

[51] Int. Cl.³ ...................... G01N 27/72; G01R 33/00
[52] U.S. Cl. .................................... 324/225; 324/237
[58] Field of Search ............... 324/225, 228, 234, 236, 324/237, 238

[56] References Cited

U.S. PATENT DOCUMENTS

| 3,585,225 | 12/1967 | Peugoet ................................ 324/225 |
| 3,611,120 | 10/1971 | Forster ................................. 324/225 |
| 3,714,558 | 1/1973 | Swanepoel ........................... 324/225 |
| 3,737,764 | 6/1973 | Dufayet ................................ 324/237 |
| 3,974,442 | 8/1976 | Savidge et al. ...................... 324/225 |

OTHER PUBLICATIONS

Mandula, "Eddy Current Inspection of Semifinished Billets-Including Corners", Sep. 1970, Iron & Steel Engineer, pp. 85–92.

Hoffman, "A New Rotating Probe Eddy Current Method for Inspecting Bar Surface", Oct. 1975, Materials Evaluation, vol. 33, No. 10, pp. 237–242.

Primary Examiner—Gerard R. Strecker
Assistant Examiner—Walter E. Snow
Attorney, Agent, or Firm—Bacon & Thomas

[57] ABSTRACT

Inspection equipment for detecting defects in the surface of steel billets or other elongate members includes high-frequency energized eddy-current surface scanning probe which transmits signals representative of the surface condition and the probe surface spacing to a dual-channel receiver.

The signals from both channels of the receiver are combined to provide outputs representative of the surface condition compensating for changes in sensitivity resulting from changes in the probe spacing during scanning.

Probes may be positioned above the plane surfaces and/or the corners of the billet. The latter being positively located through rollers which bear against the two sides of the billet which flank the edge under inspection.

5 Claims, 11 Drawing Figures

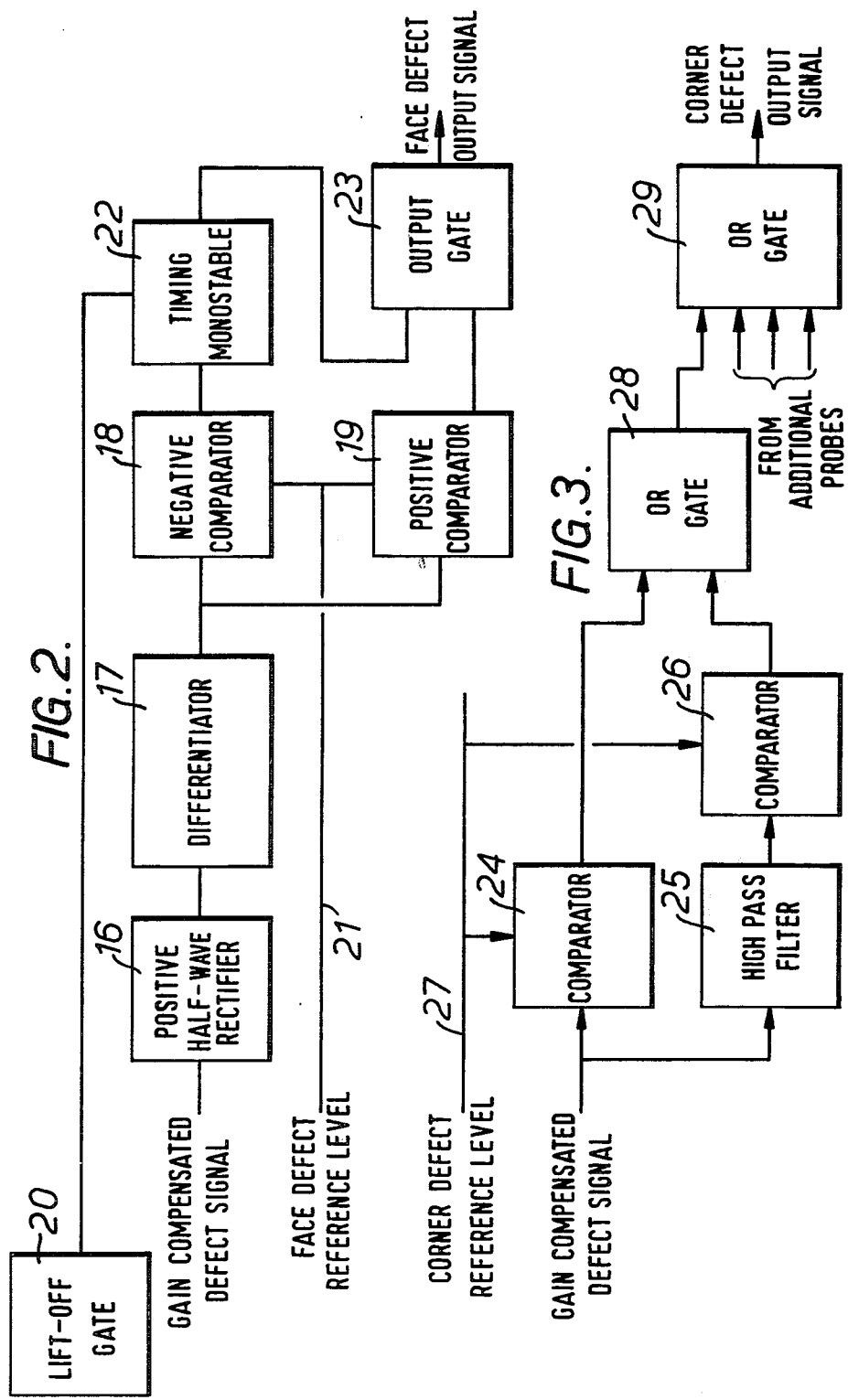

LIFT-OFF GATE

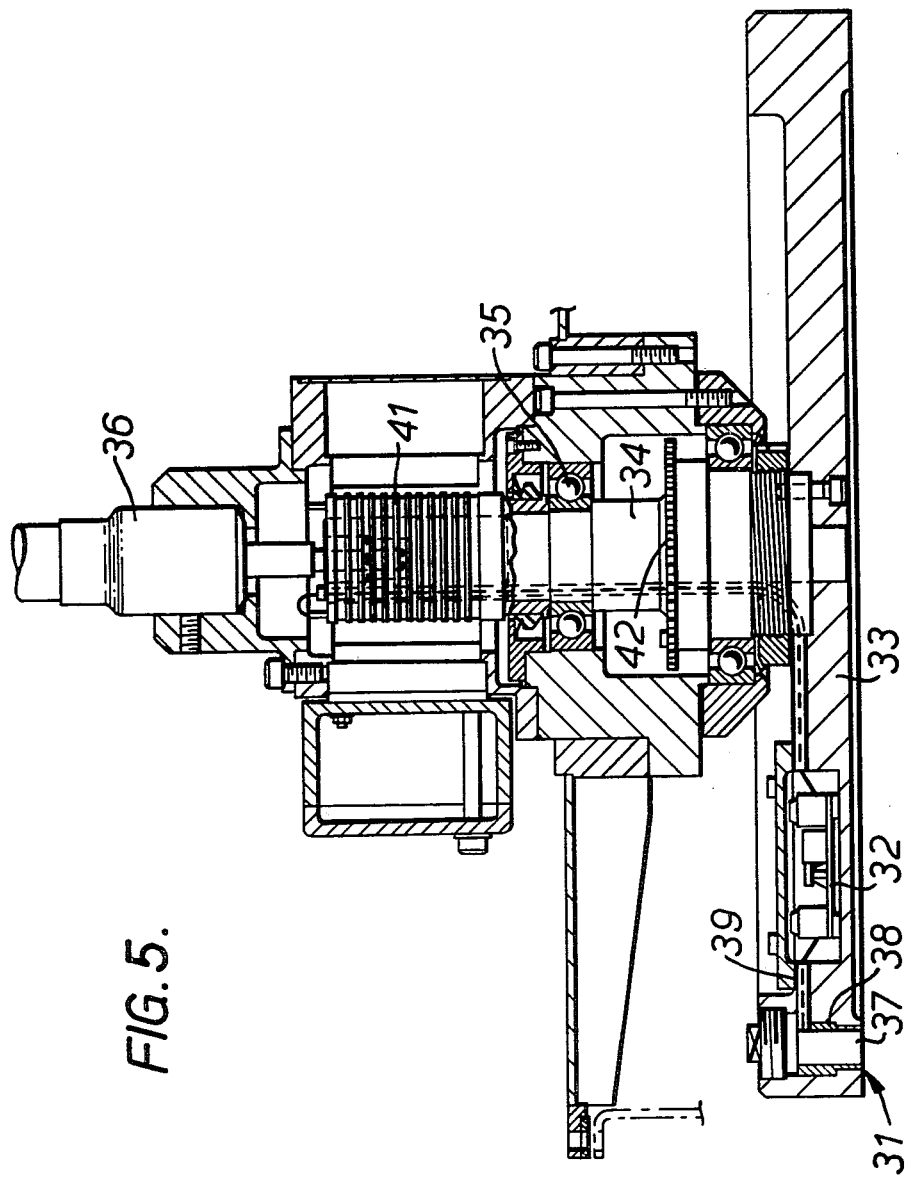

DUAL CHANNEL APPARATUS FOR DETECTING SURFACE DEFECTS IN ELONGATE METALLIC MEMBERS WITH LIFTOFF COMPENSATION

DESCRIPTION OF THE INVENTION

This invention relates to surface inspection equipment and particularly, but not exclusively, relates to such detectors for detecting defects in the surface of steel billets and for inspecting the surface of a roll either before or after dressing.

According to the present invention in one aspect there is provided apparatus for inspecting the surface of an elongate metallic member comprising a high-frequency energized eddy-current probe for scanning the surface of the member, a dual-channel receiver responsive to signals from this probe dependent on surface condition and probe surface spacing, and means for combining the signals from the two channels to give output signals representative of the surface condition compensated for changes in sensitivity resulting from changes in the probe-surface spacing during scanning.

Surface conditions detected by the inspection apparatus include surface defects, surface bruising and localised magnetic areas. The term 'defect' as used hereafter is to be taken as including all such conditions.

For rectangular section members that is to say, billets or slabs, one or more probes may be mounted in the periphery of a disc rotatable over the surface of the member about an axis perpendicular thereto. Additionally, probes may be positioned above one or more corners of the member and may be positively located through rollers which bear against the sides of the member which flank the corner under inspection. For members of circular section, eg. rod or bar, or steel mill rolls, the probe(s) may be mounted in a sensing head rotatable about the circular surface. Alternatively, the member may rotate and the sensing head remain stationary. In each case, the inspection pattern defined will be dependent upon the rotational speed of the head and the axial speed of the member relative to the head or vice versa.

The probe itself may form the inductive part of a tuned oscillator circuit thus avoiding stray capacitance problems associated with this item at the high frequencies employed, ie. 1 to 5 MHz. By incoporating the probe coil in a tuned circuit in this way the coil parameters are resolved into an in-phase component (resistance) and a quadrature component (inductance), subsequent multiplication of these components after further processing is designed to reject unwanted information to provide a sensitive response.

In a preferred arrangement the probe comprises a coil wound on to a ferrite rod mounted in a ferrite core and coupled through an oscillator circuit to a buffer amplifier which separates and directs the frequency and amplitude information derived from the oscillator circuit to the respective channels of the dual-channel receiver. Processed signals from the two channels may then be combined in a multiplier to provide defect signals compensated for changes in the spacing between the probe and the member under inspection. The compensated defect signals may then be further processed through defect recognition circuits.

According to the present invention in another aspect there is provided apparatus for inspecting the surface of an elongate metallic member which comprises a high frequency energized eddy-current probe for scanning the surface of the member and which forms the inductive part of a tuned high-frequency oscillator circuit, a buffer amplifier operable to separate frequency and amplitude contents of output signals received from the oscillator circuit and to transmit such separated signals to a dual-channel receiver, and a multiplier operable to receive processed signals from the dual-channel receiver and to combine these to provide output signals representative of the surface condition of the member compensated for changes in sensitivity resulting from changes in the probe spacing during scanning.

The use of the high frequencies employed confines the induced eddy-currents to the surface of the member under inspection to improve the resolution of detected defects and to provide greater conformity in the characteristics of different members as the frequency increases.

Figure 6:
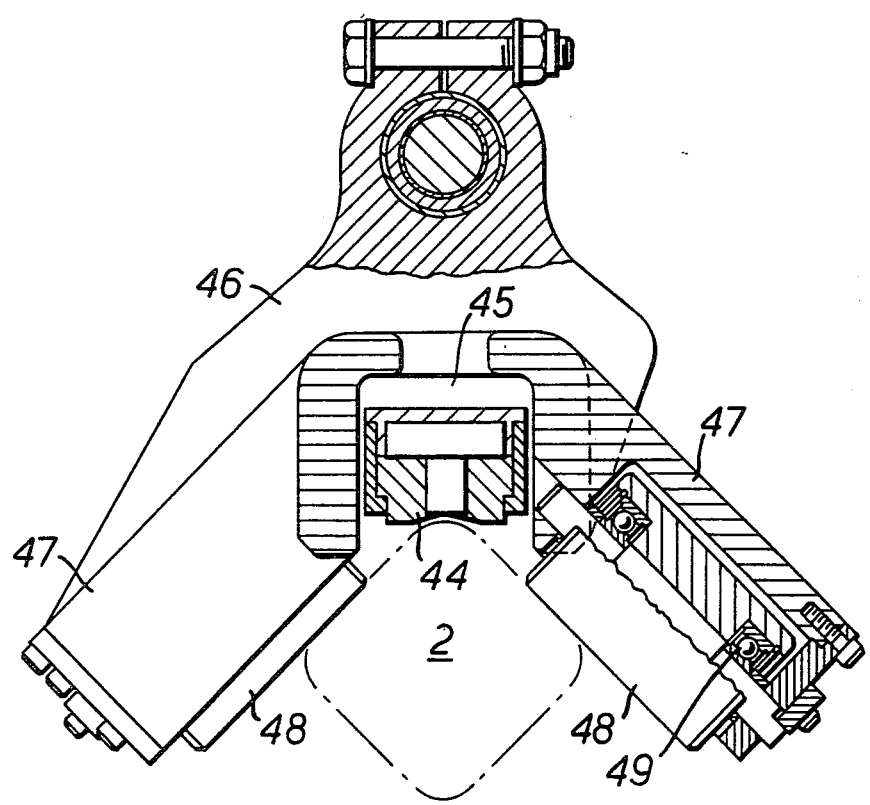

The invention will now be described by way of example with reference to the accompanying diagrammatic drawings in which:

FIGS. 1 to 3 are block circuit diagrams of apparatus according to the invention, FIGS. 4a to 4f are wave-form diagrams showing typical input and output signals processed in the apparatus illustrated in FIGS. 1 and 2, FIG. 5 shows one particular form of detector for scanning the face of a steel billet, and FIG. 6 shows one particular form of detector for scanning a corner of a square or rectangular section billet.

Referring firstly to FIG. 1 of the drawings, a coil 1 set in a probe head traverses the surface of a steel billet 2 and forms the inductive part of a tuned high-frequency oscillator circuit 3 operating at eg. 2 MHz. The oscillator circuit produces a constant current feed to the coil 1; thus- the amplitude developed across the coil is determined by the resistive properties of the coil impedance and the frequency of oscillation is determined by the reactive component of the coil impedance. Changes in the spacing between the coil and the surface of the billet 2 ('lift-off') and the surface condition of the billet consequently produce corresponding changes in the amplitude and frequency of the oscillator circuit.

Surface conditions detected by the probe include surface defects (eg. cracks), surface bruising caused by localised heating and localised magnetic areas not removed by degaussing.

Whilst the amplitude and the frequency contents of the oscillator output are both dependent on probe lift-off and defects, the amplitude content is primarily dependent on probe lift-off.

A dual channel buffer amplifier 4 separates the frequency and amplitude information derived from the oscillator 3 into two basic information channels 5,6 characteristic respectively of the defect content and probe lift-off content of output signals from the oscillator circuit 3. The channels 5,6 are capable of driving long cables which connect the probe head to remote electronic processing cabinets.

The frequency channel 5 is processed through a frequency demodulator 7 and differentiators 8,9 to provide the basic defect signal. Responses which are characteristic of true defects are enhanced by being processed in further derivative processing apparatus as will be described below with reference to FIG. 3, thereby reducing any unwanted residual signals.

The probe lift-off content of the output signal from the oscillator circuit 3, is used, subsequently to compensate the recovered surface defect signal for exponential variations in sensitivity caused by changes in the probe lift-off. The amplitude channel 6 is calibrated to a standard level in an amplifier 11 and passed to a curve shaper 12 to produce an exponential signal required for lift-off compensation.

The processed frequency and amplitude signals from channels 5,6 are applied to the inputs of a multiplier 13 in order to produce the desired defect signal free from sensitivity variations caused by changes in probe lift-off. The compensated defect output signal from the multiplier 13 is then further processed to provide an output signal truly representative of the defect in the billet surface detected by the probe. When the probe is used to scan one face of a rectangular-section billet, the output signal from the multiplier 13 is further processed through the apparatus illustrated in FIG. 2 and when used to scan corners of the billet, is further processed through the apparatus illustrated in FIG. 3.

Figure 4A:
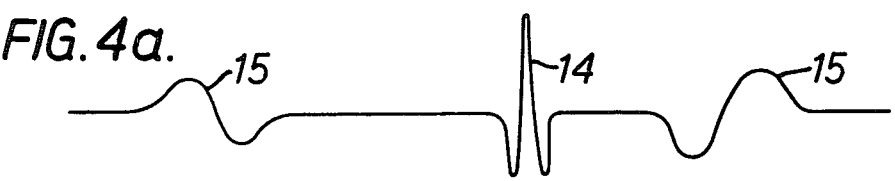

When scanning the face of the billet with a scanning disc the compensated defect signal appears as a waveform as shown in FIG. 4a. The central response 14 is typical of a normal seam defect but the two additional flanking responses 15 are produced as the probe approaches and leaves the billet surface in the corner regions of the billet. These unwanted additional responses 15 produce output signals indistinguishable from those associated with true defects unless steps are taken to recognise the differences in the wave-form resulting from these two different effects before the magnitude of the signal is measured.

Figure 4B:
Figure 4C:
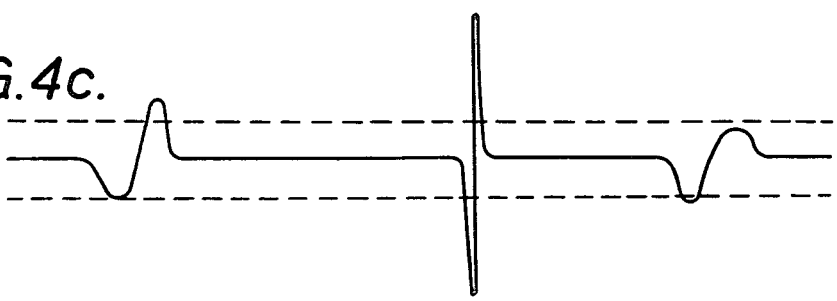
Figure 4D:

The positive responses are separated out by a positive half-wave rectifier 16 as illustrated in FIG. 2 to produce a wave-form as shown in FIG. 4b and the signal is then differentiated by differentiator 17 to produce the response shown in FIG. 4c. From examination of this wave-form it will be seen that the responses 15 associated with the billet corner signals have unequal positive and negative responses whereas the true defect signal 14 produces essentially an equal bipolar response. In addition the width of the signal responses from the true defect signal 14 are equal and well defined, whereas the positive and negative responses from the corner signals 15 are decidedly unequal. Advantage is taken of these two effects recognising true defect signals.

Figure 4E:
Figure 4F:
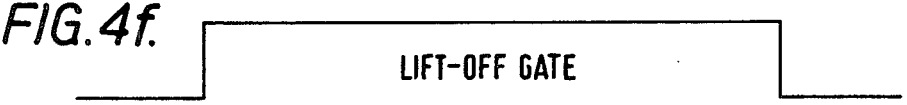

The differentiated output signal from differentiator 17 is applied to two comparators 18,19 to produce an output pulse whenever the positive or negative signal exceeds a reference level fed through a channel 21 to the comparators 18,19. A true defect signal is recognisable as one which first exceeds the negative threshold and then exceeds the positive threshold within a defined period of time to produce an output pulse having a wave-form as shown in FIG. 4e. This defined time period is produced by monostable timing circuit 22 triggered from the output of the negative comparator 18, see FIG. 4d. Triggering of the monostable timing circuit 22 is inhibited by a gate 20 whilst lift-off is outside a pre-set operating range (see FIG. 4f) further to reduce the chance of processing unwanted information. The above described circuit satisfactorily eliminates signals produced by the probe coil 1 scanning the corners of the billet to provide output signals from a gate 23 truly representative of the defect in the billet surface detected by the scanning probe.

When the corners of rectangular-section billets are examined two fundamentally different types of responses are evident, these being those associated with transverse defects and those associated with longitudinal defects. In order to separate these two components, compensated defect signals from the multiplier 13 are passed through filters so that the responses can be compared against individual thresholds. Transverse defects can be detected at higher sensitivity levels than longitudinal defects because filters for transverse defects are more selective and well defined. Indeed, it is usual to employ a defect threshold for the detection of transverse defects which is a preset fraction of that used for longitudinal defects. As illustrated in FIG. 3, filtered output signals from the multiplier 13 are transmitted as inputs to a comparator 24 and via a high pass filter 25, a comparator 26. These measured signals are compared with a preset reference signal transmitted through channel 27 and the outputs from both comparators 24,26 are combined in an 'OR-GATE' 28 to provide an output representative of the defect detected in the scanned corner of the billet. Similar procedures are adopted for each of the other probes scanning the corner under inspection and these signals are further combined in a second 'OR-GATE' 29 to produce a defect output for a specific billet corner. As for the apparatus illustrated in FIG. 2, lift-off gating ensures that information is produced only when the probe clearance is adequate.

The circuit illustrated in FIG. 3 is useful also for detecting surface bruising and localised areas of remnant magnetism in the billet.

The mechanical construction of a typical scanning head for traversing the surface of a billet is shown in FIG. 5.

In this Figure, four evenly spaced probe coils 31 (only one of which is shown) and associated oscillator circuits 32 are mounted in the periphery of a disc-shaped body 33 having a shaft 34 mounted for rotation in bearings 35 and the body is caused to rotate at a predetermined clearance (lift-off) above the billet surface. The shaft 34 is coupled to a flexible drivesystem 36. The coil in each probe is wound on a ferrite rod which is mounted in a cup shaped ferrite core 37; to screen the coil from the damping effect of any metallic holder into which the probe may be placed, the coil is then potted in a stainless shell 38. Leads 39 from the oscillator circuits 32 are channeled through the head to separate slip rings in a unit 41 carried on the rear end of the shaft 34 to couple the signals from the circuits 32 through resilient connectors bearing on the slip ring contacts to a buffer amplifier mounted adjacent the head. Output signals from the buffer amplifier (item 4 in FIG. 1) are fed to the circuitry described above. In order that the position of each probe may be identified, a toothed gear wheel 42 is mounted within the rotating assembly to allow the rotation position of any probe to be resolved with high accuracy. Four inspection heads would normally be deployed in the manner described above to scan all four faces of a square or rectangular section billet in one pass thus producing an inspection pattern dependent upon the billet throughput speed and the disc rotational speed. The mechanical construction of a typical head for scanning a corner of a billet is shown in FIG. 6.

Three probe coils 44 are mounted in a central recess 45 of a bifurcated housing 46 hiving three forks 47 (only two of which can be seen from FIG. 6) which carry rollers 48 mounted for rotation in bearings 49. The probes coils 44 are staggered in the direction of travel of the billet and are spaced so that each scans one third of the corner area under inspection. The rollers 48 are positioned to bear against the two side faces flanking the corner of the billet 2 to be inspected, two rollers on one face and one on the other face, and to position the probe coils 44 a preset distance away from the surface of the corner. As for the face scanning apparatus illustrated in FIG. 5 the probe coils 44 are connected through an oscillator circuit to a buffer amplifier such as illustrated at 4 in FIG. 1. Output signals from the coils 44 are then processed by the circuitry illustrated in FIGS. 1 and 3. For inspecting all four corners of the billet, four inspection heads would be employed each of construction as shown in FIG. 6. In this arrangement the fork of one head which bears on one face of the billet lies between the two forks of the adjacent head which bears on the same face of the billet. All four heads are mounted in trailing arm linkages.

For inspection of circular-section rolls, billets or bar, the probe coils and associated oscillator circuits are mounted in an annular head which rotates about the periphery of the billet or bar. As the feedstock under inspection passes through the head, the inspection path takes the form of a multistart spiral having a pitch dependent upon the rotational speed of the head and the throughput speed of the feedstock. Alternatively, the feedstock under inspection may be caused to rotate and the scanning head remain stationary or substantially so. When processing signals from such apparatus, the circuit described above for the elimination of 'billet edge' signals can be used to suppress probe bounce responses normally encountered with rotating probe assemblies with workpiece surface conditions such as overfill.

Although the invention has been described with reference to the particular embodiments illustrated, it is to be understood that various modifications may be made without departing from the scope of the invention. For example, details of the circuits shown may readily be changed provided that their overall function remains the same. The probe heads may also be differently designed, those shown simply being convenient for the task involved. Similarly, the scanning head may incorporate any member of probe coils suitable for the particular application in mind, the more probe coils there are, the greater the degree of surface coverage for a given rotational speed and axial speed of billet throughput.

We claim:

1. Apparatus for inspecting the surface of an elongate metallic member comprising a high-frequency energised eddy-current probe for scanning over the surface of the member, said probe forming the inductive part of a tuned high-frequency oscillator circuit in which the amplitude of the voltage developed across the probe is determined by the resistive properties of the impedance of the probe, and the frequency of oscillation of said developed voltage is determined by the reactive properties of said probe impedance, a buffer amplifier connected to receive output signals from the oscillator circuit and to transmit amplified frequency-characteristic signals to one channel of a dual-channel receiver and amplified amplitude-characteristic signals to the second channel of said dual-channel receiver, a frequency discriminator in circuit in said one channel connected to receive said frequency-characteristic signals and to transmit demodulated signals to a first input of a multiplier, a curve shaper in circuit in said second channel of said dual-channel receiver and connected to receive said amplitude-characteristic signals and to transmit gain-compensated signals to a second input of said multiplier, said input signals being processed within said multiplier to provide output signals representative of the surface condition of the member under inspection compensated for changes in sensitivity resulting from changes in the probe spacing during scanning.

2. Apparatus as claimed in claim 1 for inspecting the plane surface of an elongate metallic member of rectangular cross-section, comprising a disc-shaped probe-carrying housing mounted for rotation above the surface of the member under inspection about an axis perpendicular to said surface.

3. Apparatus as claimed in claim 2 wherein a plurality of evenly spaced probes are mounted in the periphery of the disc-shaped housing, each probe being connected through an electrical lead to a slip ring assembly operable to couple signals from the respective probe to the dual-channel receiver.

4. Apparatus as claimed in claim 1 for inspecting a corner of an elongate metallic member of rectangular cross-section, comprising a bifurcated housing having forks which carry rollers positioned to bear against the two side faces flanking the corner of the member under inspection, at least one probe being positioned within the housing between the said forks.

5. Apparatus as claimed in claim 1 for inspecting the surface of an elongate metallic member of circular cross-section comprising a probe-carrying housing mounted for rotation about the surface of the member under inspection.

* * * * *